(12) United States Patent
Shtirberg et al.

(10) Patent No.: US 12,318,211 B2
(45) Date of Patent: Jun. 3, 2025

(54) LOCATION-BASED PATTERN MATCHING OF CORONARY SINUS (CS) SIGNALS

(71) Applicant: BIOSENSE WEBSTER (ISRAEL) LTD., Yokneam (IL)

(72) Inventors: Illya Shtirberg, Nesher (IL); Lilia Suzdalnitsky, Haifa (IL); Eran David Yonai, Pardes Hana—Karkur (IL); Aviad Spitzer, Haifa (IL); Tomer Yeger, Cohavit (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 407 days.

(21) Appl. No.: 17/863,156

(22) Filed: Jul. 12, 2022

(65) Prior Publication Data
US 2024/0016435 A1 Jan. 18, 2024

(51) Int. Cl.
A61B 5/00 (2006.01)
A61B 5/06 (2006.01)
A61B 5/287 (2021.01)
A61B 5/35 (2021.01)
(Continued)

(52) U.S. Cl.
CPC .............. *A61B 5/367* (2021.01); *A61B 5/065* (2013.01); *A61B 5/287* (2021.01); *A61B 5/35* (2021.01); *A61B 5/6852* (2013.01); *A61B 5/7221* (2013.01); *A61B 34/20* (2016.02); *A61B 2034/2051* (2016.02); *A61B 2562/043* (2013.01)

(58) Field of Classification Search
None
See application file for complete search history.

(56) References Cited

U.S. PATENT DOCUMENTS

| 11,071,486 B2 | 7/2021 | Honicker |
| 11,213,235 B2 | 1/2022 | Osadchy |
| 2014/0107508 A1 | 4/2014 | Harlev |

(Continued)

FOREIGN PATENT DOCUMENTS

| AU | 2017208338 A1 | 3/2018 |
| WO | WO2018132543 A1 | 7/2018 |

OTHER PUBLICATIONS

International Search Report for corresponding PCT Appln. No. PCT/IB2023/056926 dated Oct. 27, 2023.

*Primary Examiner* — Sana Sahand (57) ABSTRACT

A method includes, during arrhythmia occurrence, acquiring multiple sets of reference coronary sinus electrophysiological (CS-EP) signals with a first catheter in coronary sinus (CS) of a heart of a patient, while measuring multiple respective reference CS locations of the first catheter. One or more intra-cardiac electrophysiological (IC-EP) signals are acquired with a second catheter located in a cardiac chamber of the heart, while acquiring actual CS-EP signal with first catheter, and while measuring an actual CS location of first catheter. Using reference CS locations, reference CS-EP signal is identified whose reference CS location is nearest to actual CS location of the first catheter. A signal-stability measure between actual CS-EP signal and identified reference CS-EP signal is estimated. If signal-stability measure is above given threshold, identified reference CS-EP is utilized to verify whether the one or more IC-EP signals acquired by the second catheter are acquired during occurrence of the arrhythmia.

16 Claims, 3 Drawing Sheets

(51) Int. Cl.
  *A61B 5/367*  (2021.01)
  *A61B 34/20*  (2016.01)

(56) References Cited

U.S. PATENT DOCUMENTS

2017/0251942 A1    9/2017  Brodnick
2018/0008203 A1*   1/2018  Iyun ..................... G16H 50/70
2020/0170525 A1    6/2020  Osadchy

* cited by examiner

LOCATION-BASED PATTERN MATCHING OF CORONARY SINUS (CS) SIGNALS

FIELD OF THE DISCLOSURE

The present disclosure relates generally to electrophysiological (EP) sensing using catheters, and particularly to EP signal acquisition using pattern matching (PM) of intra-cardiac signals.

BACKGROUND OF THE DISCLOSURE

Cardiac mapping techniques that use reference signals were previously reported in the patent literature. For example, U.S. Patent Application Publication No. 2017/0251942 describes an automatic method of determining local activation time (LAT) from at least three multi-channel cardiac electrogram signals including a mapping channel and a plurality of reference channels. The method comprises (a) storing the cardiac channel signals, (b) using the mapping-channel signal and a first reference-channel signal to compute LAT values at a plurality of mapping-channel locations, (c) monitoring the timing stability of the first reference-channel signal, and (d) if the timing stability of the monitored signal falls below a stability standard, using the signal of a second reference channel to determine LAT values. Substantial loss of LAT values is avoided in spite of loss of timing stability.

As another example, U.S. Pat. No. 11,213,235 describes a method that includes receiving (i) a plurality of electrocardiogram (ECG) signals acquired by a mapping catheter at a plurality of locations on a surface of a heart of a patient, (ii) a reference ECG signal from a reference catheter positioned at a nominal location in a coronary sinus (CS) of the patient, and (iii) position signals indicative of a position of the reference catheter in the CS. An electrophysiological (EP) map of at least part of the heart is calculated by time-referencing the ECG signals relative to the reference ECG signal. Based on the position signals, a displacement of the reference catheter from the nominal location in the CS, which distorts the time-referencing, is estimated. The distortion in the EP map is mitigated using the estimated displacement.

U.S. Pat. No. 11,071,486 describes how cardiac activation timing is mapped using a catheter-mounted roving electrode instead of a fixed (e.g., coronary sinus) electrode. The roving electrode is used to measure an initial electrophysiological signal at an initial cardiac location as a reference signal, which is defined as a reference signal. Local activation time(s) for other cardiac location(s), also measured using the catheter-mounted roving electrode, are determined relative to the reference signal. The stability of the reference signal can be monitored, such as by comparing activation rates or cycle lengths between an instantaneously-measured electrophysiological signal and the initial electrophysiological signal. Smaller differences between the two (e.g., less than about 5%) can be compensated for, while larger differences can result in redefining the reference signal.

BRIEF DESCRIPTION OF THE DRAWINGS

The present disclosure will be more fully understood from the following detailed description of the examples thereof, taken together with the drawings in which.

DETAILED DESCRIPTION OF EXAMPLES

Overview

During electrophysiological (EP) mapping, a physician may wish to capture an arrythmia event and determine its tempo-spatial distribution in a heart chamber. To this end, the physician EP maps the heart chamber with an EP-mapping catheter. However, the local nature of the EP acquisition does not allow a physician, or a processor of the EP mapping system, to determine the relevance of a given EP signal, since the relevance depends on whether the arrhythmia is actually occurring at the time the signal is acquired, or has ceased.

To ensure that the diagnostic EP signals are acquired during the occurrence of the arrhythmia, the physician may use a reference catheter, such as a coronary sinus (CS) catheter, to capture, in advance, a template of an arrhythmogenic coronary sinus electrophysiological (CS-EP) signal (also called "intra-cardiac electrocardiogram (IC-ECG)"), signal expressed during the occurrence of the arrhythmia. A processor, or the physician, can then compare any newly acquired CS reference signal taken during EP acquisition to the template, in order to verify that the mapping EP signal is clinically relevant (i.e., was acquired during an occurrence of the arrhythmia).

In this way, an EP signal acquired at a certain tissue location within the heart chamber, called hereinafter "intra-cardiac electrophysiological (IC-EP) signals," being mapped is accepted (e.g., for use in generating an EP map) on the condition that there is a good correlation between the current IC-EP (e.g., IC-ECG) signal and the CS-EP (e.g., IC-ECG template). This test, called Pattern Matching (PM), as used in IC PM, is the technique of acquiring a pattern from an IC catheter (placed mostly in the CS) rather than attempting correlation of ECG signals acquired from electrodes attached to skin, since the former method obtains more relevant arrhythmogenic patterns.

One drawback of this method is that a catheter in the CS tends to move over time. This movement causes the IC PM correlation score to drop to unusable correlation levels (in one example, to less than 75% after approximately half an hour). The drop in correlation causes the physician or system to waste time acquiring a new pattern and building a new EP map.

Examples of the present disclosure that are described herein provide a technique for achieving more accurate IC pattern matching that is less prone to unexpected correlation score drops. The disclosed technique comprises generating a pool of template IC patterns corresponding to different respective locations of the CS catheter. The pool is pre-saved to be used whenever movement of the CS catheter is detected. To this end, the processor switches between the prerecorded IC patterns to identify a pattern which was recorded at a nearest CS location to the current CS catheter location. Before using the identified pattern, the processor verifies its accuracy by running pattern matching (e.g., by comparing the correlation score between an actual pattern and the identified reference pattern to a predefined threshold PM score).

In one example, a method is therefore provided, the method comprising acquiring multiple sets of CS-EP signals with a first catheter in the CS of a heart of a patient, while measuring multiple respective reference CS locations of the first catheter (e.g., the CS Catheter defined above). One or more intra-cardiac electrophysiological (IC-EP) signals are acquired with a second catheter (e.g., the aforementioned mapping catheter) located in a cardiac chamber of the heart, while acquiring an actual CS-EP signal with the first catheter, and while measuring an actual CS location of the first catheter. Using the reference CS locations, a reference CS-EP signal is identified, whose reference CS location is nearest to the actual CS location of the first catheter. A signal-stability measure is estimated, between the actual CS-EP signal and the identified reference CS-EP signal. Finally, if the signal-stability measure is above a given threshold, the identified reference CS-EP is utilized to verify whether the one or more IC-EP signals acquired by the second catheter are acquired during an occurrence of the arrythmia.

To acquire CS catheter locations, in one example, the CS catheter includes a magnetic sensor that that is being used to measure the CS catheter location. In another example, electrical location detection may be used to track CS locations for every pattern acquired.

By introducing the disclosed feature, the user is unlikely to need reacquisition of an IC-ECG template pattern which would entail wasting time to build a new map with the new pattern. An important benefit of this method is therefore reducing time duration of the EP mapping procedure.

The technique thus includes an initial recording phase, where, prior to the EP mapping session, the user is prompted to move the CS catheter in the CS vein during the arrhythmia to record a pattern group of CS-EP template signals as a function of CS catheter position inside the CS. While moving the CS catheter, the disclosed algorithm saves the patterns and the respective CS catheter locations, in order to generate a pool of sub-pattern templates (i.e., patterns and respective locations). This phase typically takes between 10 and 30 seconds.

During EP mapping, which is performed by the EP mapping catheter inserted into the target cardiac chamber, the up-to-date location of the CS catheter is monitored so that a relevant template can be selected from the pattern group. A sub-pattern is matched automatically to the nearest CS catheter location where from the sub-pattern is measured, thus overcoming CS movement that results in a correlation score drop.

In one example, during EP mapping, the processor switches between the stored template patterns (inside the group) to select a pattern that best matches the actual CS catheter location. The switching can be initiated automatically, based on tracking movement of the CS catheter. Switching may also be triggered manually, for example based on the user identifying a degraded correlation score (e.g., a PM score falling below a predefined threshold). Alternatively, as noted above, switching between sub-patterns may not be available to the user, with the switching to another location-based Pattern Matching being done automatically only by the processor.

In some examples, during the initial recording phase, the acquired IC-ECG patterns are filtered using, for example, a local activation time (LAT) based filter that is run in the background (e.g., unavailable in user preferences) to ensure that the same arrythmia is being recorded. The filter rejects any IC-ECG pattern acquired when the LAT value on the reference signal does not match a "global" LAT value characteristic of the arrhythmia (such as of atrial flutter), up to a tolerance.

Using a group of patterns instead of a single pattern, more data points are practically acquired, as fewer data points are rejected due to falling correlations. An improvement of 60% in acquired data point count, amounting to thousands of additional successfully acquired EP data points during EP mapping, was observed experimentally, which means that, with a multi-electrode catheter, it may be possible to complete an EP map without a single correlation failure.

The provided method comprises acquiring reference CS-EP signals, such as IC-ECG signals, with multiple electrodes of a first catheter located at different respective measured CS locations in a coronary sinus (CS) of a heart of a patient, in order to generate a group of reference CS signals. One or more IC-EP signals are acquired with one or more electrodes of a second catheter located in a cardiac chamber of the heart, while acquiring IC-EP signals with the first catheter to generate an actual CS reference signal at a respective actual CS location. A respective signal-stability measure is estimated between the actual CS reference signal and the signals of the group of CS reference signals acquired at a nearest CS location to the actual CS location. If the signal-stability measure is above a given threshold, the one or more IC-EP signals acquired by the second catheter are utilized, for example, to generate EP map data points.

The signal-stability measure can be an average of stability measures of signals from the multiple electrodes, or a minimum among the stability measures. For example, assuming a set of correlation levels is calculated for signals from a set of electrodes, the measure may be an average correlation level, or the minimal correlation level among the set. If a correlation score, or a PM score, is provided, then that score may be the average or the minimal score among a set of scores calculated for the set of electrodes.

Typically, the processor is programmed in software containing a particular algorithm that enables the processor to conduct each of the processor-related steps and functions outlined above.

System Description

Figure 1:
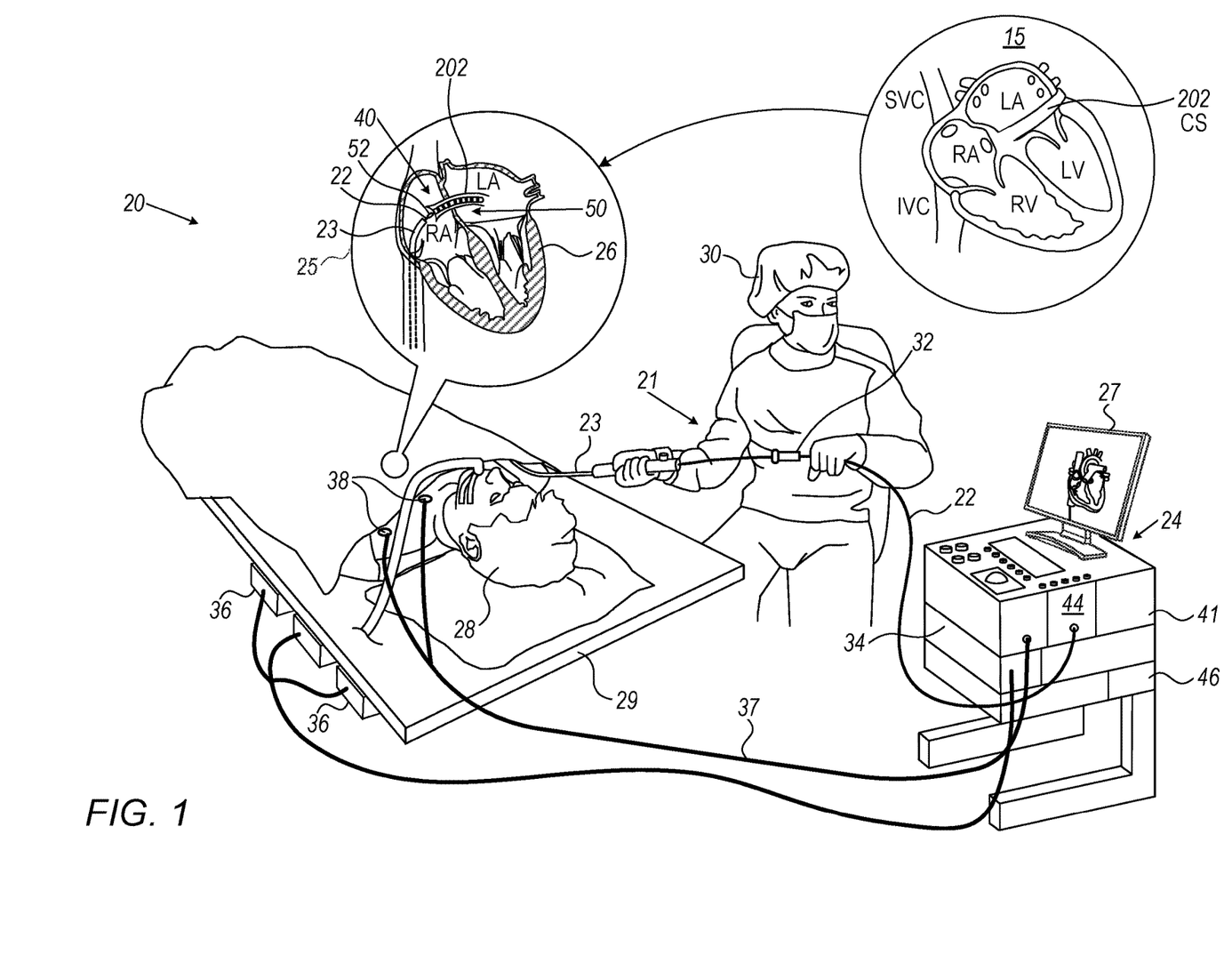
FIG. 1 is a schematic, pictorial illustration of a catheter-based electrophysiological (EP) sensing system, in accordance with an example of the present disclosure.

FIG. 1 is a schematic, pictorial illustration of a catheter 21 based electrophysiological (EP) sensing system 20, in accordance with an example of the present disclosure. Inset 15 of FIG. 1 shows a general anatomy of a heart, and, as seen, the right atrium collects deoxygenated blood from three sources, the superior vena cava (SVC), inferior vena cava (IVC), and the SC, which returns blood from the myocardium. In inset 25, catheter 21 is inserted into CS 202 to collect IC-ECG signals that may indicate atrial flutter originating either from the RA or the LA.

Catheter 21 comprises a deflectable tip section 40 that is fitted at a distal end of a shaft 22 of catheter 21 with deflectable tip section 40 comprising multiple electrodes 50. In the example described herein, Physician 30 maneuvers a sheath 23 of catheter 21 inside the RA using catheter handle 32 in an aim to insert deflectable tip section 40 into CS 202 so that, as described in FIG. 2, a distal portion of electrodes 50 overlaps the LA of heart 26 to acquire EP signals originating in the LA, while a proximal portion of electrodes 50 overlaps the RA of heart 26 to acquire EP signals originating in the RA. The IC-ECG signals may be unipolar signals, measured between electrodes 50 and surface electrodes 38, which are seen in the exemplified system as attached by wires running through a cable 37 to the chest of patient 28 laying on a table 29.

The proximal end of catheter 21 is connected to a control console 24 comprising interface circuits 44. Electrodes 50 are connected by wires running through shaft 22 interface circuits 44, where the EP signals are received and processed (e.g., digitized), and outputted to processor 41 in console 24 for analysis.

Processor 41 may further receive electrical impedance signals measured between electrodes 50 and surface electrodes 38. A method for tracking the positions of electrodes 50 using the measured impedances is implemented in various medical applications, for example in the CARTO™ system, produced by Biosense-Webster (Irvine, California) which is described in detail in U.S. Pat. No. 8,456,182, and which is assigned to the assignee of the current disclosure. This method is sometimes called Advanced Catheter Location (ACL). Console 24 drives a display 27, which shows the tracked position and/or shape of deflectable tip section 40 inside heart 26. The various signals, such as the EP signals, are stored in a memory 46.

In some examples, system 20 further comprises a magnetic location system to magnetically track the location of catheter 21 inside CS 202. To this end, console 24 further comprises a driver circuit 34 that is configured to drive fixed magnetic field generators 36. As further seen, the CS catheter 21 is fitted with a magnetic sensor 52 at the moving deflectable tip section 40. During the navigation of deflectable tip section 40, console 24 receives location signals from magnetic sensor 52, in response to magnetic fields from the fixed external field generators 36, and, from this, a processor calculates the tip location in a coordinate system of fixed magnetic field generators 36. The method of location sensing using external magnetic fields is implemented in various medical applications, for example, in the CARTO™ system, produced by Biosense Webster, which is described in detail in U.S. Pat. Nos. 6,618,612 and 6,332,089, in PCT Patent Publication WO 96/05768, and in U.S. Patent Application Publication Nos. 2002/0065455, 2003/0120150, and 2004/0068178, whose disclosures are all incorporated herein by reference.

Processor 41, shown comprised in control console 24, is typically a general-purpose computer with suitable front end and interface circuits 44 for receiving signals from catheter 21 in a left atrium of heart 26 and for controlling the other components of system 20. Processor 41 typically comprises software in memory 48 of system 20 that is programmed to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 41 runs a dedicated algorithm as disclosed herein, included in FIG. 4, that enables processor 41 to perform the disclosed steps, as further described below.

Cs Catheter Movement Inside the Cs

Figure 2:
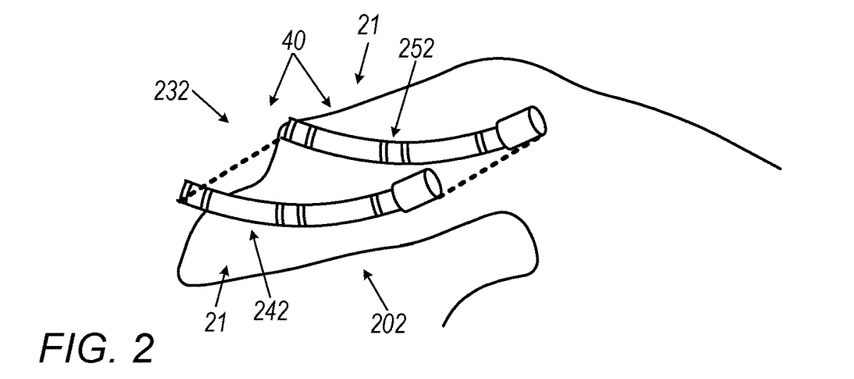
FIG. 2 is a schematic, pictorial illustration of a change in location of a coronary sinus (CS) catheter inside the CS, in accordance with an example of the present disclosure.

FIG. 2 is a schematic, pictorial illustration of a change 232 in the location of coronary sinus (CS) catheter 21 inside the CS 202, in accordance with an example of the present disclosure. In FIG. 2, deflectable tip section 40 is seen displaced (232) between two locations, e.g., former location 242 and new, actual location 252.

Such a change in location may disqualify the IC-ECG pattern for use because its PM score falls below a threshold. However, using the disclosed technique, as the new location 252 is measured, the processor switches between the stored template patterns (inside the group) to select a pattern according to the one that most closely matches the actual CS catheter location 252.

Correlated and Uncorrelated IC-ECG Signals Acquired by A Cs Catheter

Processor 41 may calculate correlation scores to IC-ECG signals acquired by catheter 21 located in the CS, using a method disclosed in U.S. Patent Application Publication No. 2021/0169359, which is assigned to the assignee of the present application, wherein a processor applies a window of interest (WOI) to the IC-ECG signals representing an entire cycle length for a single heartbeat. A pattern of interest (POI) is selected to include a portion of WOI corresponding to an arrhythmia activation. A template POI is generated that is representative of the arrhythmia activation. Subsequent electrical activity is received, weights are applied, and the subsequent electrical activity is compared with the template POI. A correlation score (also called herein "PM score") is generated.

Figure 3A:
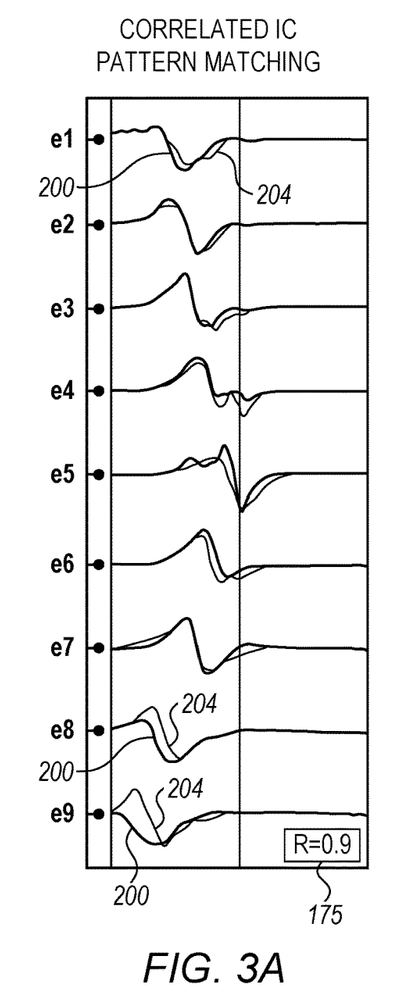
FIGS. 3A and 3B are sets of graphs showing actual intra-cardiac ECG (IC-ECG) signals that are (3A) correlated with a template pattern of IC-ECG signals, and (3B) uncorrelated with a template pattern of IC-ECG signals, the signals acquired by electrodes of the catheter of FIG. 1 placed in the CS, in accordance with some examples of the disclosure.
Figure 3B:
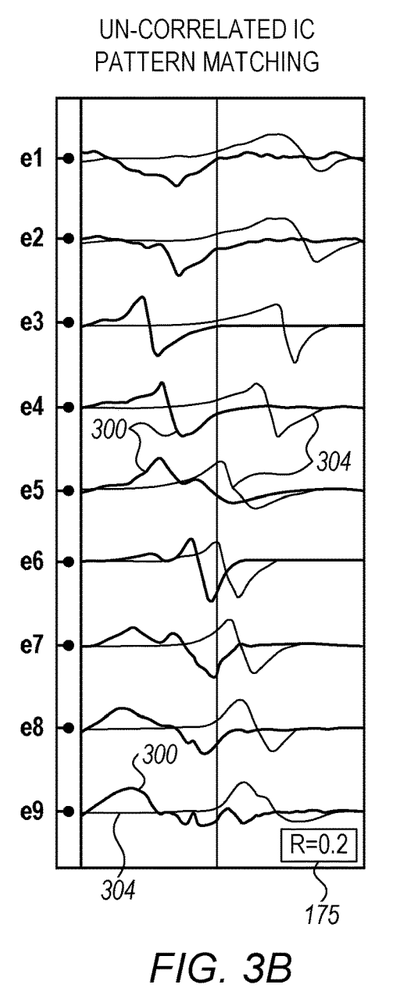

FIGS. 3A and 3B are sets of graphs showing actual IC-ECG signals 204 that are (3A) correlated with a template pattern of CS-EP signals 200, and actual CS-EP signals 304 that are (3B) uncorrelated with another template pattern of IC-ECG signals 300, with all signals (200, 204, 300, 304) acquired by electrodes 50 of the CS catheter 21 of FIG. 1 placed in CS 202, in accordance with some examples of the disclosure.

The actual CS-EP signals 204 and 304 were acquired during EP mapping. The correlation level, which can either be an average over all electrodes, or a minimum, is provided (175) on the displayed graphs. As seen, the calculated correlation level or correlation score is very high (e.g., 0.9) between CS actual and reference signals in FIG. 3A, but it is very low (e.g., 0.2) between these signals in FIG. 3B.

The lack of correlation seen in FIG. 3B may occur due to catheter 21 movement, or to the arrythmia not occurring when signals were taken. To overcome low correlation due to CS catheter movement, the processor switches between the stored template patterns (inside the group) to select a pattern according to the one that most closely matches the actual CS catheter location, as described in FIG. 4.

Figure 4:
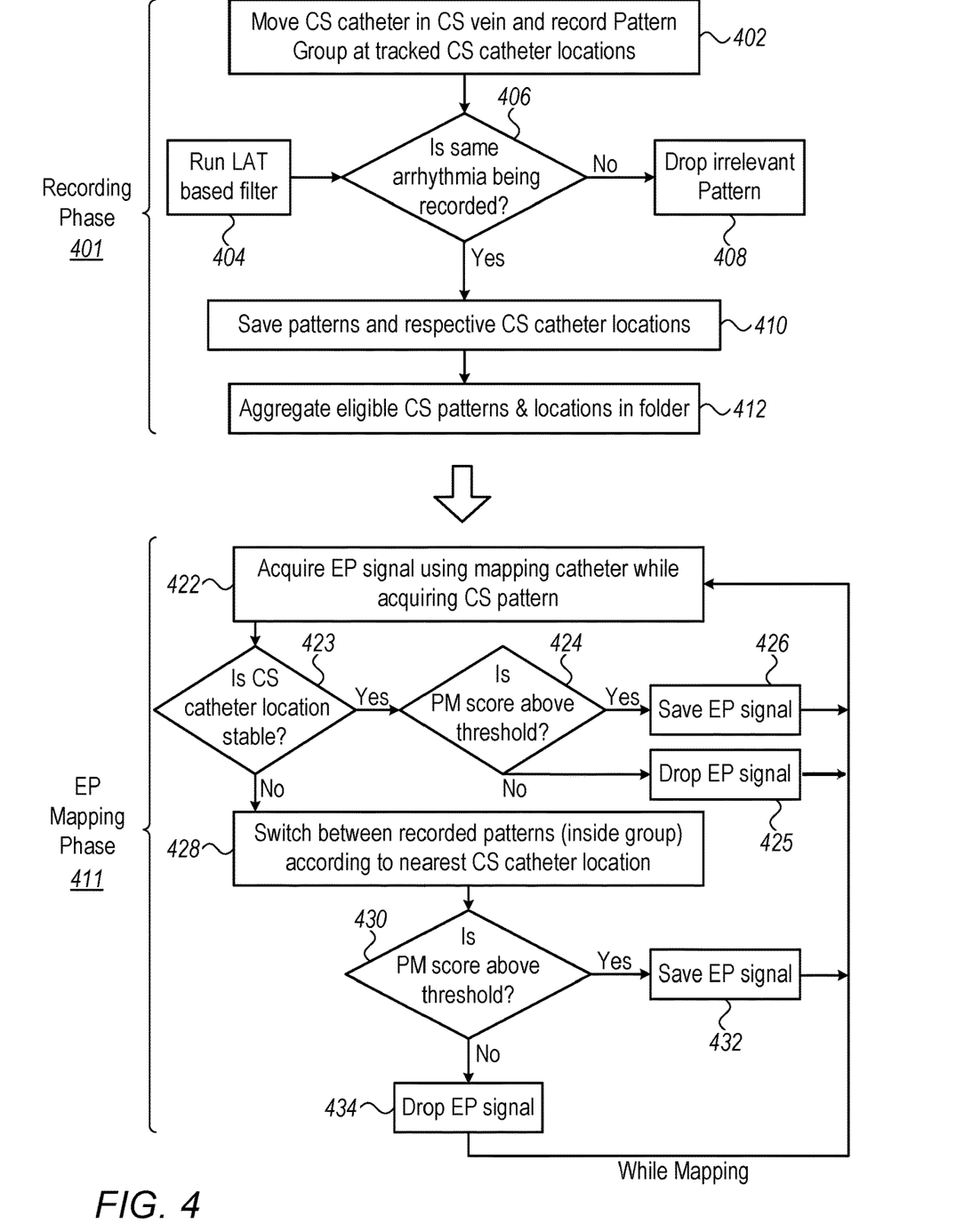
FIG. 4 is a flow chart that schematically illustrates a method of location-based pattern matching of CS IC-ECG signals, in accordance with an example of the disclosure.

Method of Location-Based Pattern Matching of CS IC-ECG Signals FIG. 4 is a flow chart that schematically illustrates a method of location-based pattern matching of CS-EP (e.g., CS IC-ECG) signals, in accordance with an example of the disclosure. The algorithm, according to the presented example, is divided into a recording phase 401 and EP mapping phase 411.

Recording phase 401 carries out a process that begins at a CS catheter moving step 402, with physician 30 moving deflectable tip section 40 of catheter 21 inside CS 202, as seen in FIG. 1, to record, one at a time, CS-EP patterns at a tracked location, such as patterns 200 or 300.

At the same time, at an LAT filtration step 404, processor 41 runs an LAT filter to verify that the CS-EP pattern is recorded when the investigated arrhythmia is active.

At a checking step 406, the processor checks if the same arrhythmia is indeed being recorded. If the answer is no, as deduced, for example, from a calculated ALT value, the processor drops the irrelevant IC-ECG pattern, at a reference pattern dropping step 408.

If the answer is yes, processor 41 saves (410) the IC-ECG pattern along with similarly eligible patterns that are recorded and checked as the catheter is moved inside CS 202.

The processor aggregates the eligible CS-EP patterns (i.e., CS IC-ECG patterns) and respective locations in a folder for use during a subsequent EP mapping session, at pattern group aggregation step 412.

ECG mapping phase 401 carries out a process that begins at a CS catheter moving step 402, with physician 30 moving deflectable tip section 40 of catheter 21 inside CS 202, as seen in FIG. 1, to record, one at a time, an IC-ECG pattern at a tracked location, such as patterns 200 or 300.

EP mapping phase 411 carries out a process that begins at EP signals acquisition step 422, when physician uses an EP mapping catheter (not shown), such as a Pentaray® catheter, to acquires IC-ECG signals at a cardiac chamber, while acquiring an actual CS pattern.

Next, the processor checks if the CS catheter was stable during acquisition, at a CS catheter position check step 423. The actual position can be determined using magnetic or electrical detection methods described above.

If the answer is "Yes," then, at correlation score checking step 424, processor 41 calculates and applies the aforementioned method to PM score the correlation between a current template of CS-EP signals in use and the actual CS pattern acquired in step 422, and compares it to a threshold (e.g., threshold=0.75). If the PM score is above threshold, the processor saves the EP signal, at EP signal saving step 426. If the PM score is below threshold, processor 41 drops the EP signal, at EP signal dropping step 425.

If the answer of step 424 is "No", meaning CS catheter location has changed, processor 41 switches between the stored template patterns (inside the group) to select a pattern according to the closest actual location of the CS catheter, at reference IC pattern selection step 428.

At second correlation score checking step 430, processor 41 calculates and applies the aforementioned method to PM score the correlation between the template of CS-EP signals selected in step 428 and the actual CS pattern acquired in step 422, and compares it to the threshold. If the PM score is now above threshold, the processor saves the EP signal, at EP signal saving step 432. If the PM score is still below threshold, processor 41 drops the EP signal, at EP signal dropping step 434. In any event, while mapping, the process returns to step 422 to acquire a new EP signal.

The flowchart of FIG. 4 is simplified for clarity and brought by way of example. In practice, there can be additional steps, such as notifications and presentation of an EP map under construction.

EXAMPLES

Example 1

A method includes, during an occurrence of an arrhythmia, acquiring multiple sets of reference coronary sinus electrophysiological (CS-EP) signals (200, 300) with a first catheter (21) in a coronary sinus (CS) (202) of a heart (26) of a patient (28), while measuring multiple respective reference CS locations of the first catheter (21). One or more intra-cardiac electrophysiological (IC-EP) signals are acquired with a second catheter located in a cardiac chamber of the heart, while acquiring an actual CS-EP signal (204, 304) with the first catheter, and while measuring an actual CS location of the first catheter. Using the reference CS locations, a reference CS-EP signal is identified whose reference CS location is nearest to the actual CS location of the first catheter (21). A signal-stability measure between the actual CS-EP signal and the identified reference CS-EP signal is estimated. If the signal-stability measure is above a given threshold, the identified reference CS-EP is utilized to verify whether the one or more IC-EP signals acquired by the second catheter are acquired during an occurrence of the arrhythmia.

Example 2

The method according to example 1, and comprising, upon verifying that the one or more IC-EP signals were acquired during the arrhythmia, using the one or more IC-EP signals to generate one or more data points of an EP map of cardiac tissue during the arrhythmia.

Example 3

The method according to any of examples 1 and 2, wherein estimating the signal-stability measure comprises estimating a level of correlation between the actual CS-EP signal (204, 304) and the identified reference CS-EP signal.

Example 4

The method according to any of examples 1 through 3, wherein estimating the signal-stability measure comprises calculating a correlation score from the level of correlation, and comparing the correlation score to a predefined threshold score.

Example 5

The method according to any of examples 1 through 4, wherein the first catheter (21) comprises a distal end comprising a linear array of electrodes (50).

Example 6

The method according to any of examples 1 through 5, wherein measuring the CS locations comprises acquiring position signals using one or more electrodes (50) of the first catheter (21), and analyzing the position signals.

Example 7

The method according to any of examples 1 through 6, wherein measuring the CS locations comprises acquiring position signals using a magnetic sensor (52) fitted at a distal end of the first catheter (21), and analyzing the position signals.

Example 8

The method according to any of examples 1 through 7, wherein the IC-EP signals are IC electrocardiogram (ECG) signals.

Example 9

A system (20) includes a first catheter (21), a second catheter, and a processor (41). The first catheter is configured to be located in a coronary sinus (CS) (202) of a heart (26) of a patient (28) and to acquire, during an occurrence of an arrhythmia, multiple sets of reference coronary sinus electrophysiological (CS-EP) signals (200, 300), while measuring multiple respective reference CS locations of the first catheter. The second catheter is configured to be located in a cardiac chamber of the heart and to acquire one or more intra-cardiac electrophysiological (IC-EP) signals while acquiring an actual CS-EP signal (204, 304) with the first catheter, and while measuring an actual CS location of the first catheter. The processor (41) is configured to (a) identify, using the reference CS locations, a reference CS-EP signal whose reference CS location is nearest to the actual CS location of the first catheter, (b) estimate a signal-stability measure between the actual CS-EP signal (204, 304) and the identified reference CS-EP signal, and (c) if the signal-stability measure is above a given threshold, utilize the identified reference CS-EP to verify whether the one or more IC-EP signals acquired by the second catheter are acquired during an occurrence of the arrhythmia.

It will be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A computer-implemented method for verifying whether intra-cardiac electrophysiological signals are acquired during an occurrence of the arrhythmia, having steps performed by a processor, comprising:
   in a recording phase, during an occurrence of an arrhythmia, acquiring multiple sets of reference coronary sinus electrophysiological (CS-EP) signals with a first catheter located in a coronary sinus (CS) of a heart of a patient, while measuring multiple respective reference CS locations of the first catheter;
   in an electrophysiological (EP) mapping phase, performed after the recording phase,
     acquiring one or more intra-cardiac electrophysiological (IC-EP) signals with a second catheter located in a cardiac chamber of the heart, while
     acquiring an actual CS-EP signal with the first catheter located in the CS, and while measuring an actual CS location of the first catheter during acquisition of the actual CS-EP signal;
   identifying a reference CS-EP signal which was acquired during the recording phase, whose reference CS location is nearest to the actual CS location of the first catheter which is acquired during the EP mapping phase, using the reference CS locations, which were measured during the recording phase;
   estimating a signal-stability measure between the actual CS-EP signal and the identified reference CS-EP signal; and
   if the signal-stability measure is above a given threshold, utilizing the identified reference CS-EP to verify whether the one or more IC-EP signals acquired by the second catheter during the EP mapping phase are acquired during an occurrence of the arrhythmia.

2. The method according to claim 1, and comprising, upon verifying that the one or more IC-EP signals were acquired during the arrhythmia, using the one or more IC-EP signals to generate one or more data points of an EP map of cardiac tissue during the arrhythmia.

3. The method according to claim 1, wherein estimating the signal-stability measure comprises estimating a level of correlation between the actual CS-EP signal and the identified reference CS-EP signal.

4. The method according to claim 3, wherein estimating the signal-stability measure comprises calculating a correlation score from the level of correlation, and comparing the correlation score to a predefined threshold score.

5. The method according to claim 1, wherein the first catheter comprises a distal end comprising a linear array of electrodes.

6. The method according to claim 1, wherein measuring the CS locations comprises acquiring position signals using one or more electrodes of the first catheter, and analyzing the position signals.

7. The method according to claim 1, wherein measuring the CS locations comprises acquiring position signals using a magnetic sensor fitted at a distal end of the first catheter, and analyzing the position signals.

8. The method according to claim 1, wherein the IC-EP signals are IC electrocardiogram (ECG) signals.

9. A system for verifying whether intra-cardiac electrophysiological signals are acquired during an occurrence of the arrhythmia, comprising:
   a first catheter, configured to be located in a coronary sinus (CS) of a heart of a patient and to acquire, in a recording phase, during an occurrence of an arrhythmia, multiple sets of reference coronary sinus electrophysiological (CS-EP) signals, while measuring multiple respective reference CS locations of the first catheter;
   a second catheter, configured to be located in a cardiac chamber of the heart and to acquire, in an electrophysiological (EP) mapping phase, performed after the recording phase, one or more intra-cardiac electrophysiological (IC-EP) signals, while acquiring an actual CS-EP signal with the first catheter located in the CS, and while measuring an actual CS location of the first catheter during acquisition of the actual CS-EP signal; and
   a processor, which is configured to:
     identify a reference CS-EP signal, which was acquired during the recording phase, whose reference CS location is nearest to the actual CS location of the first catheter which is acquired during the EP mapping phase, using the reference CS locations, which were measured during the recording phase;
     estimate a signal-stability measure between the actual CS-EP signal and the identified reference CS-EP signal; and
     if the signal-stability measure is above a given threshold, utilize the identified reference CS-EP to verify whether the one or more IC-EP signals acquired by the second catheter during the EP mapping phase are acquired during an occurrence of the arrhythmia.

10. The system according to claim 9, wherein the processor is further configured to, upon verifying that the one or more IC-EP signals were acquired during the arrhythmia, using the one or more IC-EP signals to generate one or more data points of an EP map of cardiac tissue during the arrhythmia.

11. The system according to claim 9, wherein the processor is configured to estimate the signal-stability measure by estimating a level of correlation between the actual CS-EP signal and the identified reference CS-EP signal.

12. The system according to claim 11, wherein the processor is further configured to estimate the signal-stability measure by calculating a correlation score from the level of correlation, and comparing the correlation score to a predefined threshold score.

13. The system according to claim 10, wherein the first catheter comprises a distal end comprising a linear array of electrodes.

14. The system according to claim 10, wherein measuring the CS locations comprises acquiring position signals using one or more electrodes of the first catheter, and analyzing the position signals.

15. The system according to claim 10, wherein measuring the CS locations comprises acquiring position signals using a magnetic sensor fitted at a distal end of the first catheter, and analyzing the position signals.

16. The system according to claim 10, wherein the IC-EP signals are IC electrocardiogram (ECG) signals.

* * * * *